United States Patent [19]

Bieniarz et al.

[11] Patent Number: 5,380,873
[45] Date of Patent: Jan. 10, 1995

[54] HOMOBIFUNCTIONAL AGENTS FOR COUPLING ENZYMES AND THE LIKE TO ANTIBODIES AND THE LIKE

[75] Inventors: Christopher Bieniarz, Highland Park; Christopher Welch, Urbana, both of Ill.

[73] Assignee: Abbott Laboratories, Abbott Park, Ill.

[21] Appl. No.: 999,181

[22] Filed: Dec. 22, 1992

Related U.S. Application Data

[63] Continuation of Ser. No. 600,795, Oct. 22, 1990, abandoned.

[51] Int. Cl.$^6$ ............................................. C07D 403/12
[52] U.S. Cl. .................... 548/520; 548/521; 548/546; 564/151; 564/152; 564/153; 564/159; 564/160
[58] Field of Search ............. 548/520, 521, 546; 564/58, 59, 60, 148, 151, 160, 159, 152, 153

[56] References Cited

U.S. PATENT DOCUMENTS 5,104,815  4/1992  Garner et al. .................. 548/520

FOREIGN PATENT DOCUMENTS

0314127A2  5/1989  European Pat. Off.

OTHER PUBLICATIONS

Brownlee et al—J. Chem. Soc. Chem. Commun. vol. 9, May 1986 pp. 659–660.
Lutter et al—FEBS Letters vol. 48 No. 2 (Nov. 1974) pp. 288–292.

*Primary Examiner*—Robert Gerstl
*Attorney, Agent, or Firm*—Lawrence S. Pope; Gregory W. Steele; Thomas M. Breininger

[57] ABSTRACT

A coupling agent useful in conducting immunoassays, particularly assays for B12, is disclosed. The coupling agent has the formula

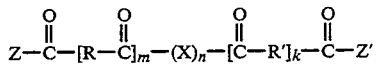

Z and Z' can be the same or different and each is

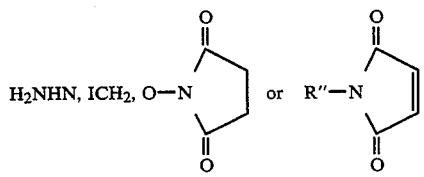

k, m and n are integers from 1 to 10, X is an alkylene group, a cycloalkylene group, an alkylcycloalkylene group, a bivalent aromatic group, or an aminoalkylene group, R and R' can be the same or different, and each is a substituted or unsubstituted aminoalkylene group having from 1 to 10 carbon atoms or a cycloalkylene or alkylcycloalkylene group having from 5 to 20 carbon atoms. Z and Z' are the same except that they can be the same or different when both are

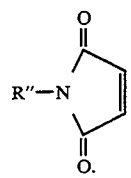

A method for purifying an aqueous intrinsic factor solution which contains R-protein is disclosed. The method involves adding to the intrinsic factor solution an amount of cobinamide sufficient to bind substantially all of the R-protein in the solution and an amount of an intrinsic factor affinity resin sufficient to bind the intrinsic factor in the solution, washing the bound cobinamide and the R-protein from the resin, eluting the intrinsic factor from the resin, and dialyzing the eluted intrinsic factor. The purified intrinsic factor can contain less than 0.004 percent cross reactivity with cobinamides, and at least 95 percent of the proteins in the (Abstract continued on next page.)

purified material can bind cobalamins. A conjugate where microparticles and the purified intrinsic factor are conjugated by a moiety from one of the foregoing coupling agents is also disclosed, as is a kit for conducting an assay for cobalamins which includes the conjugate of microparticles and purified intrinsic factor. A method for conducting an assay for cobalamins, which method involves the use of the conjugate of microparticles and purified intrinsic factor is also disclosed.

10 Claims, 6 Drawing Sheets

HOMOBIFUNCTIONAL AGENTS FOR COUPLING ENZYMES AND THE LIKE TO ANTIBODIES AND THE LIKE

This application is a continuation of application Ser. No. 07/600,795, filed Oct. 22, 1990, now abandoned.

FIELD OF THE INVENTION

This invention relates to homobifunctional agents for coupling enzymes and the like to antibodies and the like, and to enzymes and the like coupled to antibodies and the like by the homobifunctional agents. Specifically, the homobifunctional agents can be used to couple antibodies, cells, enzymes, coenzymes, proteins, haptens and small molecules to enzymes, coenzymes, antibodies, proteins, solid phases, polymers and liposomes, and the coupled compound, sometimes herein called a "conjugate", can be an antibody, a cell, an enzyme, a coenzyme, a protein, a hapten or a small molecule coupled to an enzyme, a coenzyme, an antibody, a protein, a solid phase, a polymer or a liposome.

BACKGROUND OF THE INVENTION

The following discussion of immunoassays and definitions of terms often used with respect to immunoassays are set forth herein as background to facilitate the understanding or the disclosure and claims hereof.

The term "analyte" refers to the protein, which may be, but is not necessarily, an antibody, to be detected.

The term "test sample" typically refers to a sample of body fluid such as plasma, serum, ascites, lymphatic fluids, cerebral spinal fluid, nipple fluid discharge, urine and other body fluids that may contain the analyte of interest. Optionally, the test sample can be diluted in a suitable diluent buffer, such as phosphate buffered saline with serum components, to provide a sample volume that is required by the particular immunoassay.

The term "specific binding member" refers to a member of a specific binding pair, i.e., two different molecules wherein one of the molecules through chemical or physical means specifically binds to the second molecule. In addition to antigen and antibody specific binding pairs such as the allergen and antibody pair, other specific binding pairs include biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog. If the specific binding member is an immunoreactant it can be, for example, an antibody, antigen, hapten, or complex thereof. If an antibody is used, it can be a monoclonal or polyclonal antibody, a recombinant protein or antibody, a mixture or mixtures or a fragment or fragments thereof, as well as a mixture of an antibody and other specific binding members. The details of the preparation of such antibodies and their suitability for use as specific binding members are well-known to those skilled-in-the-art.

The term "indicator reagent" refers to an assay reagent comprising a detectable label directly or indirectly attached to a specific binding member which is capable of directly or indirectly binding to the analyte and thereby indicating the presence, absence or amount of the analyte in a test sample. A variety of different indicator reagents can be formed by varying either the label or the specific binding member. In general, the indicator reagent is detected after it has formed a complex with either the analyte or a complementary specific binding member, but the unbound indicator reagent can also be detected.

The term "label" refers to any substance which is attached to a specific binding member and which is capable of producing a signal that is detectable by visual or instrumental means. Labels can include chromogens; catalysts; fluorescent compounds; chemiluminescent compounds; radioactive isotopes; direct visual labels including colloidal metallic and non-metallic particles, dye particles, enzymes or substrates, or organic polymer latex particles; liposomes or other vesicles containing signal producing substances; and the like.

Many enzymes suitable for use as labels are disclosed in U.S. Pat. No. 4,275,149, columns 19–23, herein incorporated by reference. For example, an enzyme/substrate signal producing system useful with 4-methylumbilliferyl phosphate is the enzyme alkaline phosphatase. If horseradish peroxidase is used, o-Phenylenediamine is added as an enzyme substrate to form a colored product which can be detected and/or measured visually or instrumentally.

In an alternative signal producing system, the label can be a fluorescent compound where no enzymatic manipulation of the label is required to produce a detectable signal. Fluorescent molecules such as fluorescein, coumarin, phycobiliprotein, rhodamine and their derivatives and analogs are suitable for use as labels in this system.

Another class of labels includes the visually detectable, colored particles which enable a direct colored readout of the presence or concentration of the analyte in the test sample without the need for using additional signal producing reagents. Materials for use as such particles include colloidal metals, such as gold, and dye particles as disclosed in U.S. Pat. Nos. 4,313,734 and 4,373,932. The preparation and use of non-metallic colloids, such as colloidal selenium particles, are disclosed in co-owned U.S. Pat. No. 4,954,452, which is incorporated by reference herein. Organic polymer latex particles for use as labels are disclosed in co-owned and copending U.S. patent application Ser. No. 248,858, filed Sep. 23, 1988, now allowed which is incorporated by reference herein. The selection of a particular label is not critical, so long as the label is capable of generating a detectable signal either by itself or in conjunction with one or more additional signal producing substances. The term "signal producing component" refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product. The term "capture binding member" refers to a specific binding member which can bind directly or indirectly to the analyte or indicator reagent and which is bound or is capable of being bound to a solid phase, or is capable of being precipitated, such that the capture binding member can be separated from the test sample and other assay reagents.

The term "capture reagent" refers to a capture binding member which is directly or indirectly attached to a solid phase material to enable the separation of the capture binding member, and analyte or indicator reagent that is bound thereto, from unbound analyte and assay reagents. Typically, the attachment of the capture binding member to the solid phase material is substantially irreversible and can include covalent mechanisms. A capture reagent in which a capture binding member is indirectly attached to a solid phase can be produced by reacting a coupling agent of the instant invention with both the solid phase material and the capture reagent; the product of such a reaction is an example of a "conjugate". In an agglutination assay, the capture binding member of the capture reagent can be bound to a soluble carrier material such as bovine serum albumin.

In producing a capture reagent to be used in an assay, once the capture binding member, e.g., analyte specific antibody, is immobilized upon the solid phase, the remaining surface area of the solid phase is generally blocked with a suitable protein solution, such as bovine serum albumin, to prevent non-specific binding of protein to the support. The solid support is then washed with an appropriate solution to remove any excess blocking solution and/or unbound capture binding member.

Once complex formation occurs between the assay components, the solid phase can be used as a separation mechanism. For example, the reaction mixture can be contacted with the solid phase material, and the solid phase material retains the newly formed reaction complex(es). Alternative methods can be used to perform this separation step, such as using a solid phase which itself binds to the capture binding member; affixing to the solid phase a binding member that is specific for the capture binding member; or affixing to the solid phase a reactive agent, such as a charged substance, which will attract and bind an oppositely charged substance that has been bound to the capture binding member, as disclosed in co-owned and copending U.S. patent application Ser. No. 150,278, filed Jan. 29, 1988, now Ser. No. 816,786, which is incorporated by reference herein. Either the binding member that is specific for the capture binding member or the reactive agent (e.g., a charged substance) can be bound to or chemically reacted with a coupling agent according to the invention which is also bound to or chemically reacted with the solid phase material; these are also examples of conjugates.

Assay devices can have many configurations, several of which are dependent upon the material chosen for the solid phase. The term "solid phase material"0 refers to any suitable chromatographic, bibulous, porous or capillary material or other conventional solid material, well-known to those skilled-in-the-art for use in immobilizing specific binding members. Solid phase materials can include a fiberglass, cellulose or nylon pad for use in a flow-through assay device having one or more layers containing one or more of the assay reagents; a dipstick for a dip and read assay; a test strip for chromatographic (e.g., paper or glass fiber) or thin layer chromatographic (e.g., nitrocellulose) techniques in which one or all of the reagents are contained in separate zones of a single strip of solid phase material; or an absorbent material well known to those skilled-in-the-art. The solid phase material can also include, without limitation, polyacrylamide beads, polystyrene beads or tubes, magnetic beads, a microtitre plate with one or more reaction wells, microparticles or a glass or plastic test tube. Natural, synthetic or naturally occurring materials that are synthetically modified, can be used as a solid phase material including polysaccharides, e.g., cellulose materials including paper, cellulose and cellulose derivatives such as cellulose acetate, nitrocellulose and cellulose acetate/nitrate; silica; fiberglass; inorganic materials such a deactivated alumina, diatomaceous earth or other inorganic finely divided material uniformly dispersed in a porous polymer matrix, with polymers such as vinyl chloride, vinyl chloride-propylene copolymer, and vinyl chloridevinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtitre plates; polystyrene tubes; protein binding membranes; Sephadex (Pharmacia Fine Chemicals, Inc., Piscataway, N.J.); Trisacryl (Pointet-Girard, France); silicon particles; porous fibrous matrixes; and the like. The solid phase material should have a reasonable inherent strength or strength can be provided by means of a support, and it should not interfere with the production of a detectable signal.

When the specific binding member of the capture reagent is affixed to microparticles, those particles can be retained in a column, suspended in a mixture of soluble reagents and test sample, or retained and immobilized by another solid phase base material. By "retained and immobilized" is meant that the particles, associated with the solid phase base material, are not capable of substantial movement to positions elsewhere within that material. The size of the particles is not critical, although it is preferred that the average diameter be smaller than the average pore size of the solid phase base material if such is used, and they must be of such a size that they can be suspended in a suitable liquid if they are to be used in an agglutination assay.

The term "ancillary specific binding member" refers to a specific binding member used in addition to the capture binding member and the indicator reagent which becomes a part of the detectable binding complex. One or more ancillary specific binding members can be used in an assay. For example, an ancillary specific binding member can be used in an assay where the capture binding member is capable of binding the ancillary specific binding member which is in turn capable of binding the solid phase.

It will be appreciated by those skilled-in-the-art that the selection of any given label, ancillary binding member or solid phase material is generally not critical to the present invention. The materials are chosen to optimize the results provided by the chosen assay configuration.

It has been disclosed, European Patent Application 0 221 505, published May 13, 1987, that immunogens suitable for intravenous administration can be produced by incubation with pepsin immobilized on a hydrophilic gel containing amino groups by a dicarboxylic acid disuccinimidyl ester. The disuccinimidyl ester is disclosed as having a succinimidyl group at each end of a chain having the structure

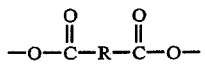

where R is a straight or branched chain alkylene radical having from 1 to 20 carbon atoms. The application specifically discloses only one such compound: adipic acid disuccinimidyl ester where R, above, is a straight chain alkylene group having 4 carbon atoms.

Various bifunctional coupling agents are commercially available, for example from Pierce, exemplary ones being disclosed in a catalog published by that company. Disuccinimidyl suberate and ethylene glycolbis(-succinimidylsuccinate) are examples of such coupling agents disclosed in the catalog. In the latter compound, R in the foregoing formula is

Cobalamins have the general structure shown in FIG. 1 of the attached drawings. While cobalamins have sometimes been referred to as vitamin B12, there are actually several different types of cobalamins which differ from each other by the R substituent shown in the FIG. 1 structure: cyanocobalamin (R=cyano), hydroxycobalamin (R=hydroxy), aquacobalamin (R=H2O), nitrocobalamin (R=NO2), 5′ deoxyadenosylcobalamin (R=5′ deoxyadenosyl), and methylcobalamin (R=methyl). Each of these cobalamins is considered generally to be a vitamin B12: cyanocobalamin (vitamin B12), hydroxycobalamin (vitamin B12a), aquacobalamin (vitamin B12b), nitrocobalamin (vitamin B12c), 5′ deoxyadenosylcobalamin (coenzyme B12), methylcobalamin (methyl B12). The various cobalamins have similar metabolic activity. Cyanocobalamin, however, is more stable than the others. The cobalamins are involved in many metabolic functions and are essential for normal growth and nutrition, hematopoiesis, production of all epithelial cells, and maintenance of myelin throughout the nervous system.

A deficiency in vitamin B12 manifests itself in ineffective hematopoiesis, inadequate myelin synthesis, inadequate maintenance of the epithelial cells of the alimentary tract, and generalized anemia. However, except for inadequate myelin synthesis, these symptoms are common to many megaloblastic anemias, regardless of cause.

To pinpoint the cause of such anemias, it is necessary to test for vitamin B12 deficiencies. There are a variety of different assays for vitamin B12: colorometric, spectroscopic, fluorometric and radioactive isotope. The most common employs a cobalt 57 radioactive isotope in lieu of the cobalt in the corrin nucleus of the vitamin B12 molecule. The radioactively labelled molecule and B12 intrinsic factor are added to a sample containing B12, and the radioactively labelled B12 and the B12 in the sample compete for binding sites on B12 intrinsic factor. The B12 intrinsic factor is associated with a solid phase, so the amount of radioactivity on the solid phase or in the sample will be proportional to the amount of B12 in the original sample. The current radioassays have obvious disadvantages inasmuch as they involve the handling, storage, and disposal of radioactive materials. Furthermore, detection can be slow.

Enzyme linked competitive binding assays have been proposed (see Bachas, Biotechnics, vol. 4, no. 1, p. 42 et seq. (1986)) for vitamin B12. However, the sensitivity of the assay was reported to be 1355 pg/ml while the normal range for vitamin B12 in human serum is from 150-900 pg/ml. Clearly, such an assay cannot be used to test vitamin B12 deficiency since it reportedly cannot even detect vitamin B12 at normal ranges in human serum.

BRIEF DESCRIPTION OF THE PRESENT INVENTION

Figure 1:
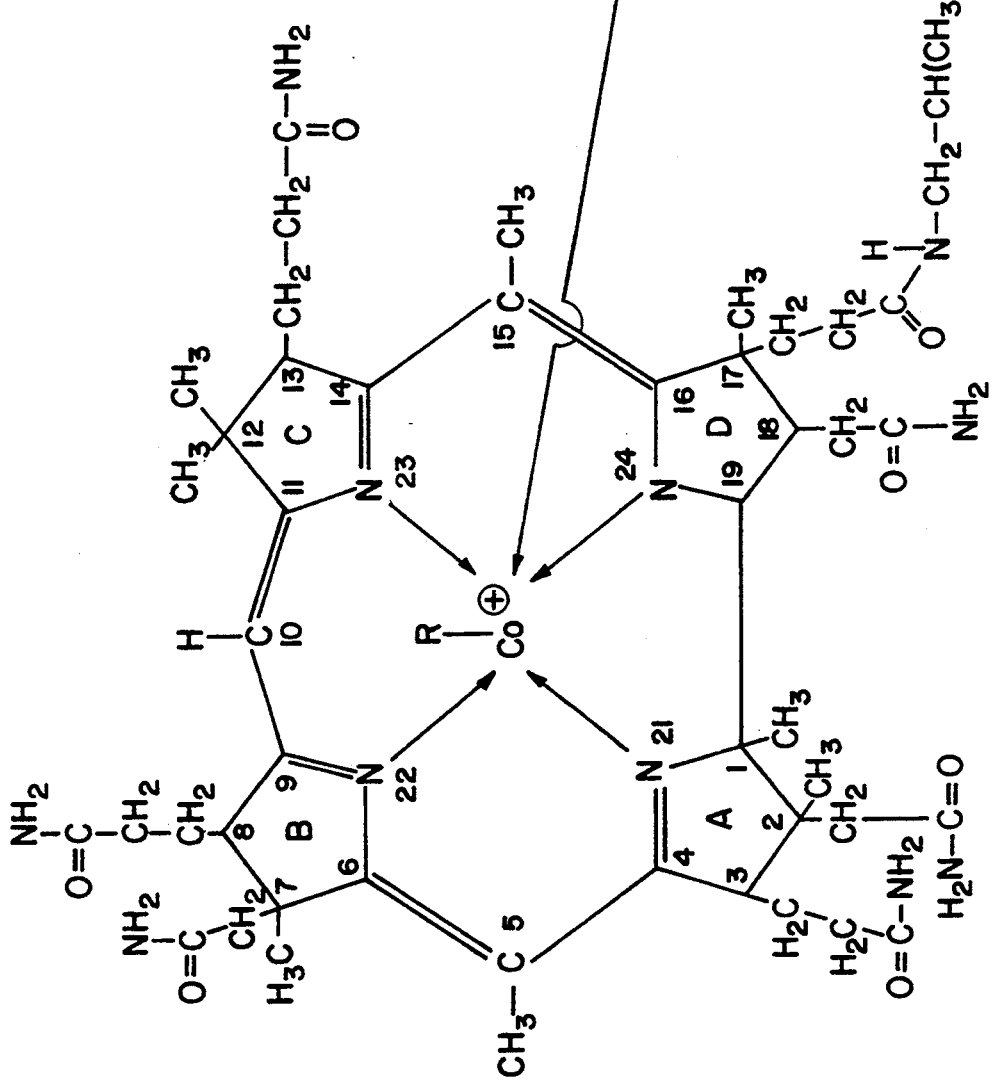
FIG. 1 is a formula showing the general structure of cobalamins.
Figure 1:
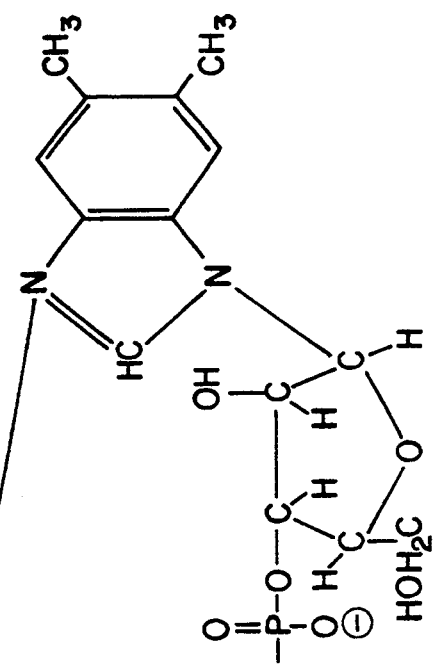
Figure 2:
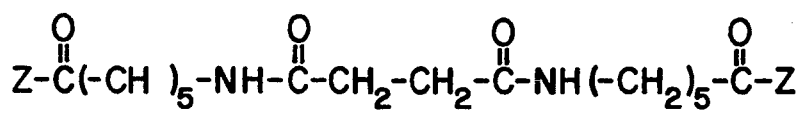
FIG. 2 is a formula showing the structure of a preferred family of compounds according to the invention.
Figure 3:
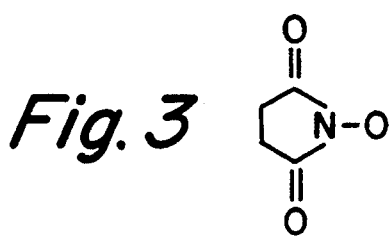
FIG. 3 is a formula showing the structure of preferred endgroups in the family of compounds of FIG. 2.

The instant invention is based upon the discovery of a disuccinimidyl compound which is an 18 atom homobifunctional linker having the structure of FIG. 2 of the drawings, where Z has the structure of FIG. 3. The invention is also based upon the further discovery that the sensitivity of an immunoassay for vitamin B12 is unexpectedly increased when a conjugate of intrinsic factor linked to microparticles by the foregoing compound is used in conducting the assay.

DESCRIPTION OF THE PREFERRED EMBODIMENTS

The invention will be more fully understood from the following examples, which constitute the best modes presently contemplated by the inventors. It is to be understood, however, that the examples are presented solely for the purpose of illustration, and are not to be construed as limiting.

As used herein, and in the appended claims, the terms "percent" and "parts" refer to percent and parts by weight, unless otherwise indicated; g means gram or grams; mg means milligram or milligrams; ng means nanogram or nanograms; pg means picogram or picograms; cm means centimeter or centimeters; mm means millimeter or millimeters; L means liter or liters; $\mu$L means microliter or microliters; m/o means mole percent, and equals 100 times the number of moles of the constituent designated in a composition divided by the total number of moles in the composition; v/v means percent by volume; w/v means weight per unit of volume, and is in terms of g/L; M means molar and equals the number of gram moles of a solute in one liter of a solution; $\mu$M means micromolar and equals the number of microgram moles in one liter of a solution; mM means millimolar and equals the number of milligram moles of a solute in one liter of a solution; N means normal, and equals the number of gram equivalents of a solute in one liter of solution; and $\mu$N means micronormal and equals the number of microgram equivalents of a solute in one liter of solution. All temperatures are in °C., unless otherwise indicated.

Figure 4:
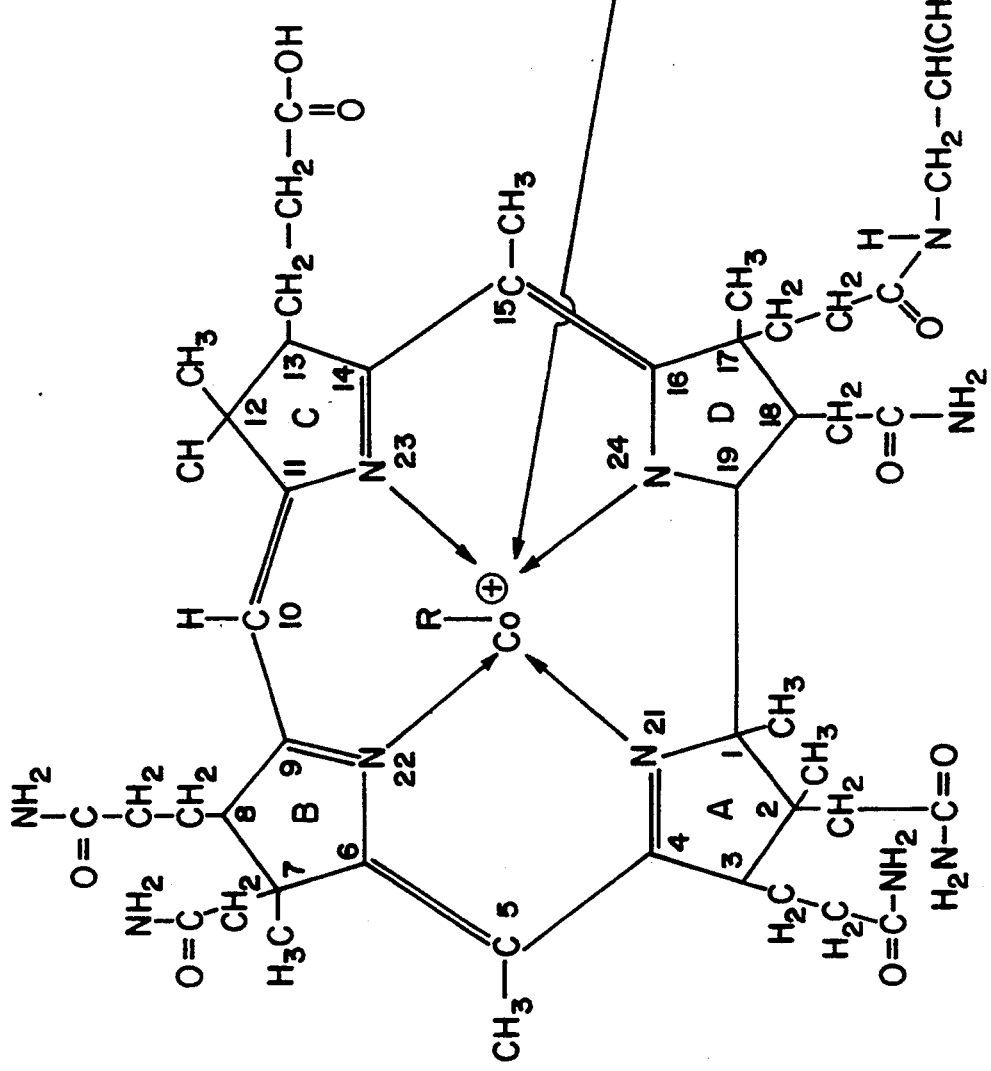
FIG. 4 is a formula showing the structure of a "red fraction" whose preparation is described herein, and is named "CARBOXYLATED B-12".

Example 1 describes the production of the 18 atom homobifunctional linker having the structure of FIG. 2. Example 2 describes the use of the 18 atom homobifunctional linker to bind alkaline phosphatase to "B12A-MINE", a compound having the structure of FIG. 4 of the attached drawings, except that the substituent attached to the 13 carbon in the C ring has the structure

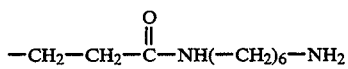

The production of the B12 AMINE is described below, as an introduction to Examples 1 and 2.

SYNTHESIS OF B12 AMINE

The B12 AMINE to which reference is made above was produced by acid hydrolyzing 2.2 g cyanocobalamin, isolating the monocarboxylic acids which were produced, separating one of the acids, and coupling the separated acid to 1,6-diamino hexane. The cyanocobalamin was added to 300 mL 0.8 M phosphoric acid and heated for six hours at 70' in the dark under a nitrogen blanket. The reaction mixture was applied to a washed ion exchange resin packed in a column; unbound derivatives were eluted; and the bound B12 acids were eluted with methanol and concentrated by rotary evaporation. The ion exchange resin used is one that is available under the trade designation AMBERLITE XAD-2. The individual B12 acids were then separated on a DE-52 Cellulose column, washed with NaOH, HCl, NaOAc, and equilibrated to pH 5.0 with deionized water. The sample was then added to a 4×75 cm column, and slowly eluted. After two days, a single red band containing unreactive corrinoid was removed with distilled water. The B12 monoacids were eluted with 0.05 percent acetic acid. Three peaks were eluted in 36 hours. Each band was collected and concentrated by rotary evaporation. Fractions which contained red material were pooled, while orange-yellow fractions were discarded. A radioassay was used to test the red fractions for reactivity. Mass spectroscopy, C13 NMR and HPLC were used to characterize the red fractions; they were found to have the structure of FIG. 4 of the attached drawings ("MONOCARBOXYLATED B12"); that is, they were carboxylated in position 13 on the C ring.

The B12 AMINE was then produced from 63 mg MONOCARBOXYLATED B12, 0.2554 g 1,6-hexyl diamine and 88.8 mg 1-ethyl-3-(3-dimethylaminopropyl)-carbodiimide CEDAC). The MONOCARBOXYLATED B12 and the 1,6-hexyl diamine were dissolved in 13 mL distilled water; the pH of the solution was adjusted to 6.0 with 1N HCl; the EDAC was added; and the reaction mixture was stirred for about 16 hours under a nitrogen blanket [Tetsuo Toraya, *J. Biol. Chem.*, 255; 3520–3525 (1980)]. The reaction mixture was concentrated by rotary evaporation and purified by HPLC [Tetsuo Toraya, *Biochem.*, 18:417–426 (1979)]. The B12 AMINE was purified on a C-18 (Magnum 9) column using a solvent system composed of 20 v/v methanol and 80 v/v 1 percent aqueous acetic acid at an initial flow rate of 4 ml per minute; after 80 minutes the flow rate was increased to 6 ml per minute. The product was identified as B12 AMINE.

EXAMPLE 1

Figure 7:
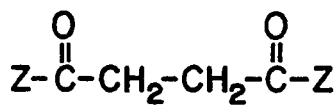
FIG. 7 is a formula for a family of active esters, one of which is produced as an intermediate in the procedure described herein as Example 1.

Synthesis of the 18 Atom Homobifunctional Linker (A) Synthesis of ester intermediate A disuccinimidyl ester intermediate was first produced from 8.16 g N-hydroxysuccinimide dissolved in 200 mL dimethylformamide, 7.17 g triethylamine and 5.0 g succinyl chloride. The triethylamine was added to the dimethylformamide solution under a nitrogen blanket. Stirring was commenced and was continued while the succinyl chloride was added slowly and for eight hours after the addition was complete. The precipitate which formed was separated from the reaction mixture by filtration, and was dried under high vacuum, yielding crude product which was triturated with 50 ml chloroform and dried in an argon stream under high vacuum, yielding 8.52 g pure white powder which was identified as the disuccinimidyl ester intermediate, a compound which has the structure of FIG. 7 of the attached drawings where Z has the structure of FIG. 3.

(B) Synthesis of linker

The 18 atom homobifunctional linker was then synthesized from 5.0 g disuccinimidyl ester intermediate dissolved in 150 ml dry dimethylformamide, 4.20 g of 6-aminocaproic acid and 6.93 g of dicyclohexylcarbodiimide. The 6-aminocaproic acid was added to the dimethylformamide solution, and the resulting reaction mixture was stirred under a nitrogen blanket for three hours at room temperature of about 22°. The dicyclohexylcarbodiimide was then added, and the reaction mixture was stirred under a nitrogen blanket for about 16 hours at room temperature. Dicyclohexyl urea precipitate which had formed was then separated from the reaction mixture by filtration, and dimethylformamide was evaporated from the filtrate under reduced pressure. Trituration with ether followed by drying under high vacuum yielded 7.94 g 18 atom homobifunctional linker.

EXAMPLE 2

Production of B12: Alkaline Phosphatase Conjugate

A conjugate was prepared from (1) 0.173 mL 0.82 mM B12 AMINE solution in 50 v/v dimethylformamide and dimethylsulfoxide,
(2) 0.142 mL 1.88 mM 18 atom homobifunctional linker solution in 50 v/v dimethylformamide and dimethylsulfoxide,
(3) 1.0 mL alkaline phosphatase (Boehringer Mannheim; 10 mg/mL) that had been dialyzed in 50 mM potassium phosphate buffer (pH 7.4) containing 0.1 mM zinc chloride, and
(4) 0.0749 mL 50 v/v dimethyl-formamide and dimethylsulfoxide.

Figure 8:
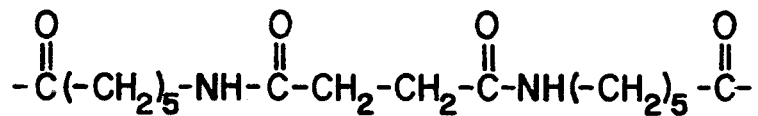
FIG. 8 is a formula showing the structure of a group by which B12 molecules are linked to alkaline phosphatase molecules in a B12 alkaline phosphatase conjugate produced as described in Example 2 hereof.

The B12 AMINE solution, the 18 atom homobifunctional linker solution and the 50 v/v dimethylformamide and dimethylsulfoxide were mixed in a glass vial and allowed to react at room temperature of about 22° for 30 minutes. The reaction mixture was then added to the dialyzed alkaline phosphatase, mixed gently, and allowed to stand for about 20 hours at 4°. The reaction mixture was separated on Sephadex G 50–100 (1.2×44 cm) using 50 mM tris(hydroxymethyl)-aminomethane ("TRIS"; pH 7.4) in deionized water which additionally contained 1.0 mg mole per liter magnesium chloride and 0.10 mg mole per liter zinc chloride. The appropriate fractions were pooled and dialyzed against 1000 ml TRIS (pH 7.4) in deionized water which additionally contained 1.0 mg mole per liter magnesium chloride and 0.10 mg mole per liter zinc chloride. The product was a B12/alkaline phosphatase conjugate in which B12 molecules were linked to alkaline phosphatase molecules by groups which had the structure of FIG. 8 of the attached drawings, the Z groups of FIG. 2 having been displaced during preparation of the conjugate. The B12/alkaline phosphatase conjugate was then diluted to a desired concentration to produce an "Enzyme-B12 Conjugate Working Solution".

Example 3, below, describes the use of the linker produced as described in Example 1 to bind purified intrinsic factor to treated microparticles. The preparation of purified intrinsic factor and of the treated microparticles to which the 18 atom homobifunctional linker of Example 1 bound the purified intrinsic factor are described below as an introduction to Example 3.

PREPARATION OF PURIFIED INTRINSIC FACTOR

About 40 pig duodenum were washed and cut into small pieces. The pieces were blended, acidified with perchloric acid to pH 1.0, and mixed for one hour. The large pieces were removed by centrifugation, and the supernatant was neutralized with 5N KOH solution in deionized water. After about 16 hours at 4° a precipitate had formed. The top 90 percent of the supernatant was aspirated and filtered through celite to remove lipid. The intrinsic factor in the clear filtrate was purified by affinity chromatography on an affinity column having a mixture of e and d B12 carboxyl derivatives ligated to cyanogen bromide sepharose 4b.

The non-specifically bound protein was removed by washing the column with 4 M NaCl solution in aleionized water, and then with 50 mM potassium phosphate buffer in deionized water. The intrinsic factor was eluted with 3.8 M Guanidine-HCl. The initial intrinsic factor fraction eluted from the column contained the intrinsic factor selected for use in the assays of this invention; later fractions yielded assays with lesser performance. The intrinsic factor in the desired fractions was tested for the presence of R proteins which bind many corrinoid ring-containing compounds (i.e. cobinamides) including but not limited to cobalamins. Once the intrinsic factor was tested (by radioassay using B12 cobalt 57) to contain less than 0.004 percent cross-reactivity with cobinamides, the intrinsic factor was exhaustively dialyzed with several changes of deionized water. The first fraction, affinity purified in this manner ("Purified Intrinsic Factor"), has been found to contain proteins of which at least 85% bind cobalamins. Less than about 85 percent functional purity was found to yield assays with impaired sensitivity.

TREATMENT OF MICROPARTICLES

A 0.5 g portion of a resin which is commercially available under the trade designation BIORAD BIO-REX MSX 501 (D) was washed several times with deionized water. A 1 mL portion of amino microparticles (SERADYNE, average diameter 0.26 μm; average parking area 390 angstroms$^2$ per amine group) and about 1 mL deionized water were then mixed with the resin, and the mixture was rotated for one hour at room temperature. The resin was allowed to settle, and the microparticles were decanted. Another 1 mL addition of deionized water was made to the resin and, after mixing, the microparticles were again decanted. The water rinse, mix and decant steps were repeated twice, and deionized water was added to the decanted microparticles to bring the microparticle solids content to 7.5 percent ("Treated Microparticles").

EXAMPLE 3

Microparticle Functionalization

A microparticle/intrinsic factor conjugate was produced from 300 μL Treated Microparticles, 600 μL Purified Intrinsic Factor solution which contained 38 μg per mL intrinsic factor and 33 μL of a dimethylformamide solution which contained 1.0 mg per mL 18 atom homobifunctional linker produced as described in Example 1 (B). The microparticles and the dimethylformamide solution of the 18 atom homobifunctional were charged to a small plastic vial, and the vial was rotated for 30 minutes; the intrinsic factor was then charged, and the vial was rotated at room temperature of about 22° for 16 hours to produce the intrinsic factor/microparticle conjugate. Before use, the conjugate was washed twice with a 0.05 percent solution in deionized water of a surfactant that is commercially available under the trade designation TWEEN 20 and twice with a 0.05 M solution of TRIS (pH 7.4) in deionized water. An "Intrinsic Factor-Microparticle Conjugate, 18 Atom Linker" was then produced by diluting one part by volume of the intrinsic factor/microparticle conjugate with 250 parts by volume of a particle diluent which was a 0.8 m TRIS solution (pH 7.4) in deionized water which also contained 1 percent bovine serum albumen, 0.1 percent NaN$_3$, 0.01 percent of a surfactant that is commercially available under the trade designation TWEEN 20, and 0.4 g mole per liter sucrose.

Examples 4 and 5 describe the derivation of a standard curve showing signal as a function of cyanocobalamin concentration in standard solutions when enzyme linked B12 assays were performed on a fully automated machine (ABBOTT IMx ® analyzer) and the use of the standard curve to assay unknown samples for cobalamin. The Enzyme-B12 Conjugate Working Solution, the Intrinsic Factor-Microparticle Working Conjugate, 18 Atom Linker, and a "Working Substrate Indicator" were used in carrying out the procedures of Examples 4 and 5. The Working Substrate Indicator was a 100 mM solution of 2-amino-2-methyl-1-propanol (pH 10.3) which also contained 1mg mole per L $MgCl_2$, 4 mg moles per L tetramisole, 1.2 mg moles per L 4-methylumbelliferone-phosphate ("MUP") and 0.1 percent $NaN_3$.

ASSAY PROTOCOL USED IN PERFORMING ENZYME LINKED B12 ASSAY

A standard or a serum sample was denatured at 34° for 8 minutes by adding cobinamide, a thiol reagent such as x-monothioglycerol and NaOH until the standard or sample contained 0.3 g equivalent per L sodium hydroxide (the purpose of this step was to dissociate B12 from serum binding proteins). The denatured solution was then neutralized with the Intrinsic Factor-Microparticle Working Conjugate, and the neutralized composition was incubated for 15 minutes at room temperature. The incubated composition was then deposited on a separation material surface, which was an IMx ® disposable reaction cell sold by Abbott Laboratories, North Chicago, Ill.; B12 bound to intrinsic factor conjugated to the microparticles was retained on the separation material surface, while B12 that was not so bound could be washed away. The separation material surface was then washed with a 50 mM TRIS (pH 7.4) solution in deionized water to free it of unbound B12. A 50 μL portion of the Enzyme-B12 Conjugate Working Solution was added to the separation material surface to bind free intrinsic factor sites. The separation material surface was again washed with the 50 mM TRIS (pH 7.4) solution in deionized water, after which a 50 μL portion of the Working Substrate Indicator was added and the separation material surface was excited with radiation having a wavelength of 362 nm. MUP is hydrolyzed by alkaline phosphatase, releasing 4-methylumbelliferone, which fluoresces when excited by radiation having a wavelength of 362 nm, emitting radiation having a wavelength of 448 nm. The reading given by the IMx ® instrument was the initial intensity per unit of time of the emission at a wavelength of 448 nm when the alkaline phosphatase substrate indicator was added to the separation material surface. The readings from patient serum samples were compared with the curve to determine B12 content.

EXAMPLE 4

The foregoing protocol was used to determine signal as a function of cyanocobalamin concentration in standards prepared by diluting USP cyanocobalamin in 50 mM TRIS solution (pH 7.4) in deionized water which also contained 1 percent bovine serum albumen, 0.2 percent $NaN_3$, 100 mg moles per L of NaCl, 1.0 mg mole per L of $MgCl_2$ and 0.1 mg mole per L $ZnCl_2$. The standards contained 0, 62.5, 125, 250, 1000, and 2000 pg/mL cyanocobalamin. The IMx ® instrument readings from the standard samples gave data for a curve showing readings as a function of B12 content.

EXAMPLE 5

The foregoing protocol was used to determine the signal from various patient samples. It has been found that the assay is capable of detecting as little as 38 pg per mL B12. Patient serum samples (n=136) were assayed as described above, and in radioassay apparatus that is commercially available from Beeton Dickinson (Orangeberg, N.Y.) under the designation SimulTrac ™. A correlation curve was calculated from the data from the two test methods, the slope of the curve was found to be 1.01, while the correlation coefficient (R) was 0.99.

Example 6, below, describes the synthesis of N-hydroxysuccinimidyltricaproamidocyclohexylmethylmaleimide from N-(carbocyclohexylmethyl) maleimide, 6-aminocaproic acid, dicyclohexylcarbodiimide and N-hydroxysuccinimide, and the synthesis from N-hydroxysuccinimidyltricaproamidocyclohexylmethylmaleimide of a 68 atom homobifunctional linker having the structure of FIG. 13 of the attached drawings where Z' has the structure of FIG. 11, and $C_6H_{10}$ is 1,4-cyclohexylene.

EXAMPLE 6

(A) Preparation of N-hydroxysuccinimidylcaproamidocyclohexylmethylmaleimide

Figure 11:
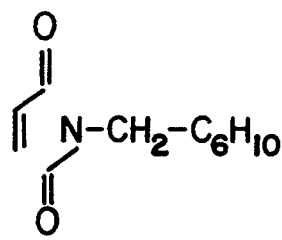
FIG. 11 is a formula showing another structure of preferred endgroups in compounds of the instant invention.
Figure 14:
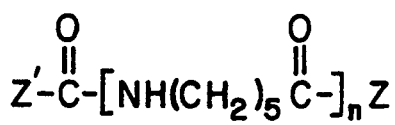
FIG. 14 is a formula showing the structure of intermediates from which compounds having the structure of FIG. 13 can be produced.
Figure 15:
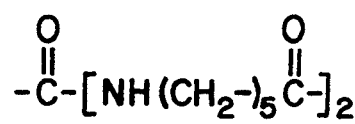

An N-hydroxysuccinimidylcaproamidocyclohexylmethylmaleimide, a compound having the structure of FIG. 14 of the attached drawings where Z has the structure of FIG. 3, Z' has the structure of FIG. 11, n is 1, and $C_6H_{10}$ is 1,4-cyclohexyl, was first produced from a solution of 100 mg N-(4-carboxycyclohexylmethyl) maleimide in dry dimethylformamide, 39.23 mg 6-aminocaproic acid, 67.8 mg dicyclohexylcarbodiimide and 37.8 mg N-hydroxysuccinimide. The N-(4-carboxycyclohexylmethyl) maleimide was produced from trans-4-(aminomethyl)-cyclohexanecarboxylic acid (Aldrich Chemical Co.) by the method of Yoshitake et al. (*J. Biochem.*, 101:395–399 (1979)). A nitrogen atmosphere was established in a flask above the N-(4-carboxycyclohexylmethyl maleimide solution, and the 6-aminocaproic acid was added to the flask. The reaction mixture was then stirred under nitrogen at room temperature of about 22° for 16 hours, after which time the dicyclohexylcarbodiimide and the N-hydroxysuccinimide were added to the flask. Stirring at room temperature was continued for an additional 6 hours, after which time dicyclohexylurea which had precipitated was removed from the reaction mixture by filtration, and the dimethylformamide was evaporated under reduced pressure from the filtrate. A tacky solid which remained was purified by flash chromatography on silica gel (5v/v methanol in chloroform), yielding 71 mg N-hydroxysuccinimidylcaproamidocyclohexylmethylmaleimide, a white solid which has the indicated formula.

(B) Preparation of N-hydroxysuccinimidyldicaproamidocyclohexylmethylmaleimide

An N-hydroxysuccinimidyldicaproamidocyclohexylmethylmaleimide, a compound having the structure of FIG. 14 of the attached drawings where Z has the structure of FIG. 3, Z' has the structure of FIG. 11, n is 2, and $C_6H_{10}$ is 1,4-cyclohexyl, was then produced from a solution of 100 mg N-hydroxysuccinimidylcaproamidocyclohexylmethylmaleimide in 1 ml dry dimethylformamide, 29.3 mg 6-aminocaproie acid and 50.7 mg dicyelohexylcarbodiimide. A nitrogen atmosphere was established in a flask above the N-hydroxysuccinimidylcaproamidocyclohexylmethylmaleimide solution, and the 6-aminocaproic acid was added to the flask. The reaction mixture was then stirred under nitrogen at room temperature of about 22° for 16 hours, after which time the dicyclohexylcarbodiimide was added to the flask. Stirring at room temperature was continued for an additional 6 hours, after which time dicyclohexylurea which has precipitated was removed from the reaction mixture by filtration, and the dimethylformamide was evaporated under reduced pressure from the filtrate. A tacky solid which remained was purified by flash chromatography on silica gel (10 v/v methanol in chloroform), yielding 60 mg of the N-hydroxysuccinimidyldicaproamidocyclohexylmethylmaleimide, which has the indicated formula.

(C) Preparation of N-hydroxysuccinimidyltricaproamidocyclohexylmethylmaleimide

An N-hydroxysuccinimidyltricaproamidocyclohexylmethylmaleimide, a compound having the structure of FIG. 14 of the attached drawings where Z has the structure of FIG. 3, Z' has the structure of FIG. 11, n is 3, and $C_6H_{10}$ is 1,4-cyclohexyl, was then produced from a solution of 100 mg N-hydroxysuceinimidyldicaproamidocyclohexylmethylmaleimide in 2 ml dry dimethylformamide, 23.4 mg 6-aminocaproic acid and 40.5 mg dicyelohexylearbodiimide. A nitrogen atmosphere was established in a flask above the N-hydroxysuccinimidyldicaproamidocyclohexylmethylmaleimide solution, and the 6-aminocaproie acid was added to the flask. The reaction mixture was then stirred under nitrogen at room temperature of about 22° for 16 hours, after which time the dieyclohexylcarbodiimide was added to the flask. Stirring at room temperature was continued for an additional 6 hours, after which time dicyclohexylurea which had precipitated was removed from the reaction mixture by filtration, and the dimethylformamide was evaporated under reduced pressure from the filtrate. A tacky solid which remained was purified by flash chromatography on silica gel (10v/v methanol in chloroform), yielding 60 mg of the N-hydroxysuccinimidyltricaproamidocyclohexylmethylmaleimide, a white solid which has the indicated formula.

(D) Preparation of the 68 atom homobifunctional linker

Figure 13:
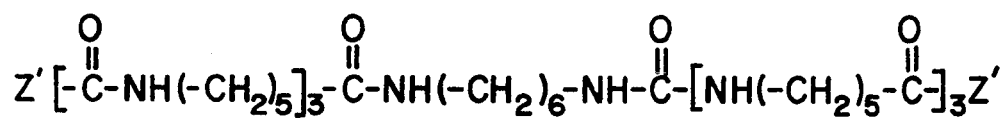
FIG. 13 is a formula showing the structure of still another preferred family of compounds according to the invention.

The 68 atom homobifunctional linker, a compound having the structure of FIG. 13 where Z' has the structure of FIG. 11 and —$C_6H_{10}$ is 1,4-eyclohexyl, can be produced at room temperature of about 22° from a solution of 0.2342 g 1,6-hexanediamine in 3 mL dry dimethylformamide and a solution of 2.695 g N-hydroxysuccinimidyltricaproamidocyclohexylmethylmaleimide in 10 mL dry dimethylformamide. The N-hydroxysuccinimidyltricaproamidocyclohexylmethylmaleimide solution is poured rapidly into the hexanediamine solution, with vigorous stirring. Stirring is continued for about two hours, after which time the dimethylformamide is evaporated, and the residue is washed three times with 15 mL portions of a 50v/v acetone in methanol solvent, and dried under reduced pressure to yield the desired product.

Example 7 describes the use of a 23 atom heterobifunctional linker produced as described in Example 6 (B) to bind purified intrinsic factor to treated microparticles. The preparations of purified intrinsic factor and of the treated microparticles to which the 23 atom heterobifunctional linker of Example 6 (B) bound the purified intrinsic factor are described above, as an introduction to Example 3.

EXAMPLE 7

Microparticle Functionalization

A microparticle/intrinsic factor conjugate was produced by combining Treated Microparticles, 700 μL Purified Intrinsic Factor solution which contained 38 μg per mL intrinsic factor and 80 μg of the 23 atom heterobifunctional linker produced as described in Example 3 (B) in 17.5 mM triethanolamine butter (pH 8.0) to produce 1 mL of a solution which contained 0.6 percent of the microparticles. The solution which resulted was mixed for 2 hours in the dark at room temperature of about 22°. After incubation, the particles were pelletted and washed several times in mild detergent/50 mM TRIS buffer solution, homogenized to ensure uniform particle size distribution, and diluted to the desired concentration ("Intrinsic Factor-Microparticle Conjugate, 23 Atom Linker").

EXAMPLE 8

Figure 6:
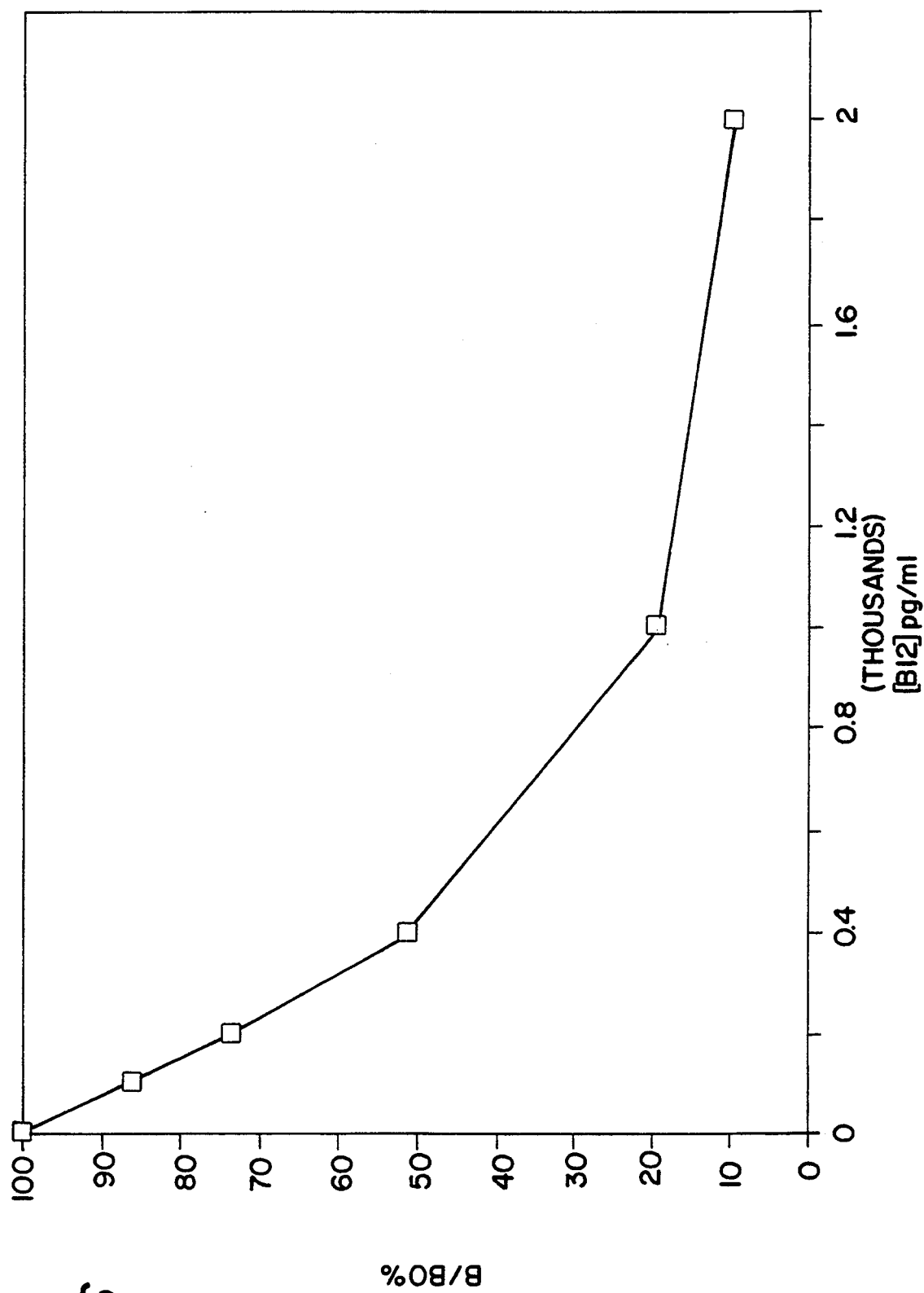
FIG. 6 is a curve showing instrument readings as a function of cyanocobalamin concentration in standard solutions prepared as described herein.

The procedure of Example 4 was repeated, except that the Intrinsic Factor-Microparticle Conjugate, 23 Atom Linker was substituted for the 18 Atom Linker. FIG. 6 of the attached drawings is a curve showing instrument readings as a function of B12 content as determined by this procedure.

EXAMPLE 9

Figure 5:
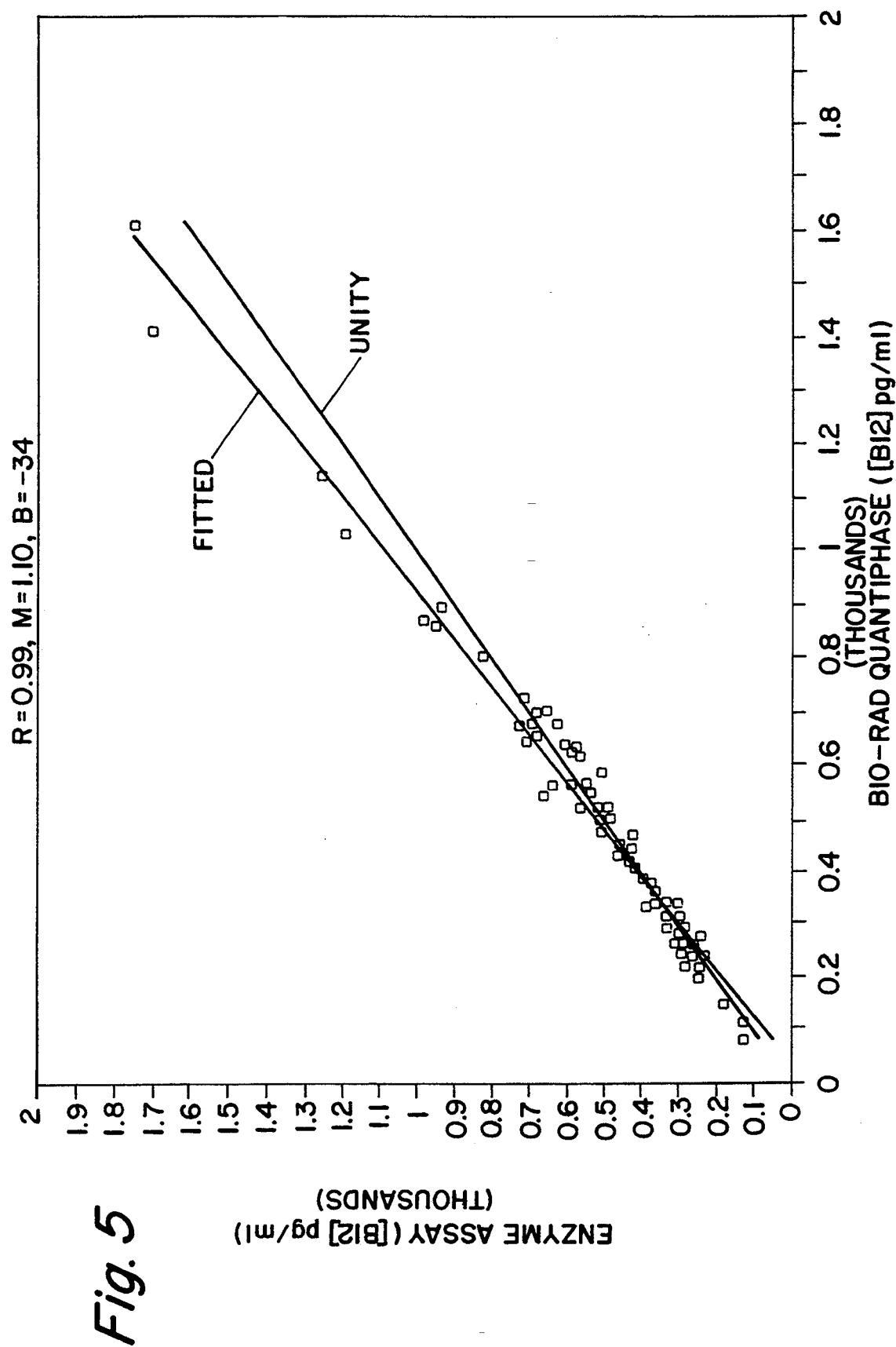
FIG. 5 is a plot of enzyme assay determinations of B12 against "BIO-RAD QUANTIPHASE" determinations of B12 in the same samples.

The procedure of Example 5 was also repeated, except that the Intrinsic Factor-Microparticle Conjugate, 23 Atom Linker was substituted for the 18 Atom Linker. It was found that the assay was capable of detecting less than 60 pg per mL B12, based on a calculation using two times the standard deviation of multiple runs of the zero standard. Patient serum samples (n=76) were assayed as described above, and in radioassay apparatus that is commercially available under the designation BIORAD, Quantaphase ™ radioassay. The correlation curve, FIG. 5 of the attached drawings, was calculated from the data from the two test methods; the slope of the curve was found to be 1.10, while the correlation coefficient (R) was 0.99.

Various other linkers according to the invention have been produced by the procedures described above and modifications thereof. Representative ones of those preparations are described in the following Examples.

EXAMPLE 10

A 22 atom bis (hydrazide) homobifunctional linker was produced from 0.50 g 18 atom bifunctional linker produced as described in Example 1 (B) dissolved in 5 ml dry methanol and 0.14 g hydrazine hydrate dissolved in 2 ml methanol. The hydrazine hydrate solution was poured into a flask and cooled to 0°; magnetic stirring was commenced, and was continued during the slow addition of the linker solution and for 30 minutes after the addition was complete. The contents of the flask were kept at 0° during the addition of the linker solution and were allowed to warm to room temperature of about 22° during the following 30 minutes. The reaction solution was then filtered through a sintered glass funnel and chromatographed on a silica gel column, using a gradient of 0.5 to 20v/v methanol in chloroform. The fractions which contained the bis (hydrazide) homobifunctional linker were collected and dried, yielding 0.21 g of the desired compound, which had the formula of FIG. 2 of the attached drawings where Z is $H_2NHN$. The compound was identified by NMR.

EXAMPLE 11

A bis (iodoacetyl) 26 atom homobifunctional linker was produced at room temperature of about 22° from 3 mL of a methanol solution which contained 0.15 g bis (hydrazide) homobifunctional linker (Example 10) and 3 mL of a methanol solution which contained 0.15 g iodoacetic acid N-hydroxysuccinimide ester. A flask which contained the bis (hydrazide) homobifunctional linker solution was placed in the dark, and stirring of the solution was commenced. The iodoacetic acid N-hydroxysuccinimide ester solution was added slowly to the flask; stirring was continued during the addition and for about 1 hour after the addition was complete. The solution was then chromatographed on a short silica gel column using 0.5 to 10v/v methanol in chloroform. The solvent was then evaporated from the fractions which contained the desired product, leaving 0.06 g bis (iodoacetyl) 26 atom homobifunctional linker, which had the structure of FIG. 2 of the attached drawings where Z has the structure of FIG. 9.

EXAMPLE 12

Figure 10:
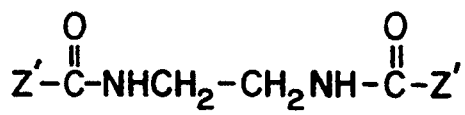
FIG. 10 is a formula showing the structure of a second preferred family of compounds according to the invention.

A bis (maleimide) 22 atom homobifunctional linker was produced at room temperature from a solution of 0.668 g succinimidyl 4-(N-maleimidylmethyl)cyclohexane-1-carboxylate dissolved in 5 mL dry dimethylformamide, 0.200 g fresh triethylamine and 0.060 g ethylenediamine. The succinimidyl 4-(N-maleimidylmethyl) cyclohexane-1-carboxylate solution was charged to a 100 mL round bottom flask. Stirring was commenced, and was continued during the addition of the triethylamine and of the ethylenediamine and for one hour after the addition was complete (a copious precipitate formed two minutes after the addition of the triethylamine and of the ethylenediamine was complete). The precipitate was then recovered by filtration, washed with water/methanol and dried. The product was identified by NMR as the bis (maleimide) 22 atom homobifunctional linker having the structure of FIG. 10 of the attached drawings where Z" has the structure of FIG. 11, and $C_6H_{10}$ is 1,4-cyclohexylene.

Figure 12:
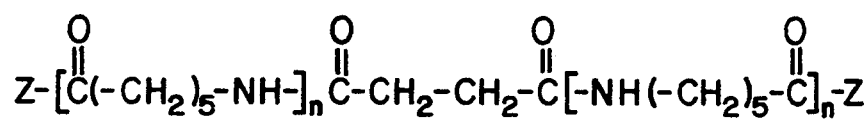
FIG. 12 is a formula showing the structure of another preferred family of compounds according to the invention.

Example 13 describes the synthesis of a homobifunctional linker according to the invention which has the structure of FIG. 12 of the attached drawings where n is 2 and Z has the structure of FIG. 3.

EXAMPLE 13

The homobifunctional linker having the structure of FIG. 12 can be synthesized from 13.6 g 18 atom homobifunctional linker [Example 1 (B)] dissolved in 410 ml dry dimethylformamide, 6.65 g 6-aminocaproic acid and 10.4 g dicyclohexylcarbodiimide. The 6-aminocaproic acid is added to the dimethylformamide solution, and the resulting reaction mixture is stirred under a nitrogen blanket for three hours at room temperature of about 22°. The dicyclohexylcarbodiimide is then added, and the reaction mixture is stirred under a nitrogen blanket for about 16 hours at room temperature. Dicyclohexyl urea precipitate which forms is then separated from the reaction mixture by filtration, and dimethylformamide is evaporated from the filtrate under reduced pressure. Trituration with ether followed by drying under high vacuum yields the indicated homobifunctional linker.

It will be appreciated from the foregoing examples that various changes and modifications can be made from the specific details of the invention as disclosed in the foregoing examples without departing from the spirit and scope thereof. For example, while the synthesis of an 18 atom homobifunctional linker is described in Example 1 (B) from a disuccinimidyl ester intermediate and 6-aminocaproic acid, an equivalent amount of various other aminoacids can be substituted for the 6-aminocaproic acid to produce other linkers having different numbers of atoms. Examples of aminoacids that can be so substituted include glycine, 3-amino-propionic acid, 4-amino-n-butyric acid, 5-amino-n-valeric acid, 7-amino-n-heptoic acid, 8-amino-n-caprylic acid, 9-amino-n-nonylic acid and 10-amino-n-capric acid. Similarly, two different ones of the aminoacids can be reacted with the disuccinimidyl ester intermediate to produce linkers containing two different aminoalkyl groups.

In addition, the procedures of parts (A), (B) and (C) of Example 6 can be carried out using equivalent amounts of any of the amino acids named in the preceding paragraph to produce other N-hydroxysuccinimidyltriamidocyclohexylmethylmaleimides which can then be converted to homobifunctional linkers by the procedure of Example 6 (D), and the N-hydroxysuccinimidyldiamidocyclohexylmethylmaleimides of Example 6 (B) can also be converted to homobifunctional linkers by the procedure of Example 6 (D). Similarly, other aliamines can be substituted for the 1,6-hexanediamine in the procedure of Example 6 (D) to produce other linkers. Examples of aliamines that can be so substituted include ones having the formula

where x is an integer from 2 to 10.

Accordingly, it will be appreciated that the instant invention, in one aspect, is a family of compounds having the formula:

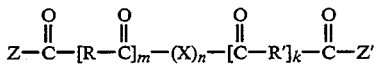

where Z and Z' are the same and each is

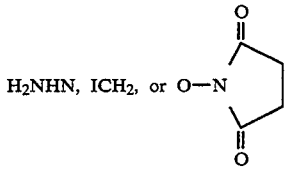

or having the formula

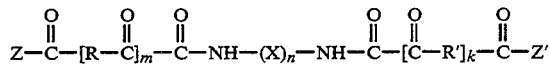

where Z and Z' are the same and each is $H_2NHN$ or $ICH_2$, or where Z and Z' are the same or different, and each is

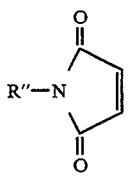

where R" is an alkylene group having from 2 to 10 carbon atoms or a cycloalkylene or alkylcycloalkylene group having from 5 to 20 carbon atoms, and wherein, in both cases, k, m and n are integers from 3 to 10, X is an alkylene group, a cycloalkylene group, an alkyl cycloalkylene group, a bivalent carbocyclic aromatic group, an amino group or an aminoalkylene group, R and R' can be the same or different, and each is a substituted or unsubstituted aminoalkylene group having from 1 to 10 carbons in a straight chain. and R" is an alkylene group having from 2 to 10 carbon atoms or a cyeloalkylene or alkylcycloalkylene group having from 5 to 20 carbon atoms.

Similarly, in a preferred aspect, the invention is a family of compounds having the structure

Figure 9:
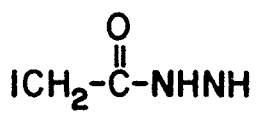
FIG. 9 is a formula showing the structure of other preferred endgroups in compounds of the instant invention.

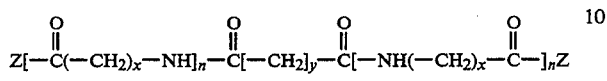

where x is an integer from 3 to 10, y is an integer from 3 to 10, n is an integer from 1 to 10, and Z is $H_2NHN$ or has the structure of one of FIGS. 3 and 9 of the attached drawings.

Likewise, in another preferred aspect, the invention is a family of compounds having the structure

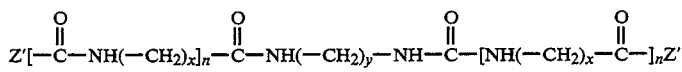

where x is an integer from 1 to 10, y is an integer from 2 to 10, n is an integer from 1 to 10, and Z is $H_2NHN$ or has the structure of one of FIGS. 9 and 11 of the attached drawings.

Other changes and modifications will be apparent to one skilled in the art, and can be made without departing from the spirit and scope of the invention as defined in the attached claims.

We claim:

1. A coupling agent having the formula

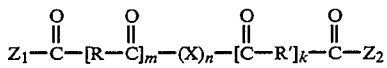

where $Z_1$ and $Z_2$ are the same when they are

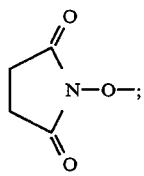

$Z_1$ and $Z_2$ may be the same or different when they are

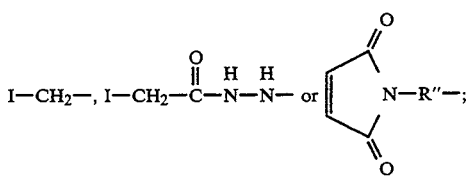

k, m and n are integers from 1 to 10;

X is an alkylene group, a cycloalkylene group, an alkylcycloalkylene group, a bivalent carbocyclic aromatic group, or an aminoalkylene group;

R and R' may be the same or different, and each is a substituted or unsubstituted $C_1$-$C_{10}$ straight chain aminoalkylene; and R" is a $C_2$-$C_{10}$ alkylene or a $C_5$-$C_{20}$ cycloalkylene or alkylcycloalkylene.

2. A coupling agent having the formula

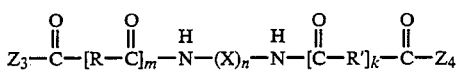

where $Z_3$ and $Z_4$ may be the same or different and are

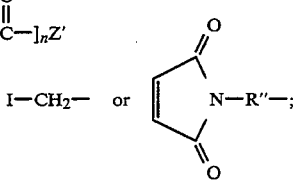

k and m are integers from 0 to 10;

n is an integer from 1 to 10;

X is an alkylene group, a cycloalkylene group, an alkyl cycloalkylene group, a bivalent carbocyclic aromatic group;

R and R' may be the same or different, and each is a substituted or unsubstituted $C_1$-$C_{10}$ straight chain aminoalkylene; and R" is a $C_2$-$C_{10}$ alkylene or a $C_5$-$C_{20}$ cycloalkylene or alkylcycloalkylene.

3. A coupling agent having the formula

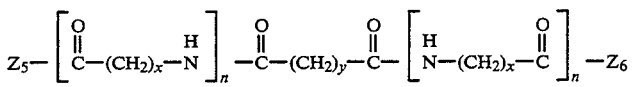

where x and n are integers from 1 to 10;

y is an integer from 2 to 1 0; and $Z_5$ and $Z_6$ may be the same or different and are

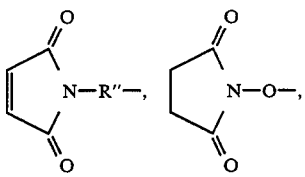

4. A coupling agent according to claim 1 where $Z_1$ and $Z_2$ are

7. A coupling agent according to claim 4 which is

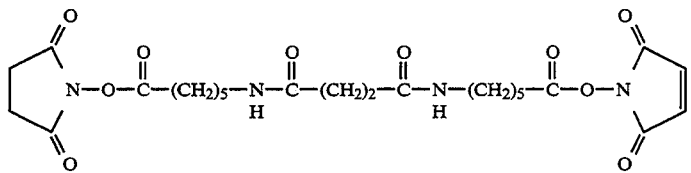

8. A coupling agent according to claim 4 which is

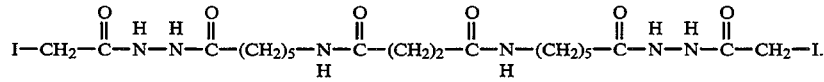

9. A coupling agent according to claim 2 which is

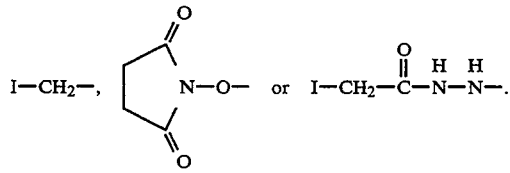

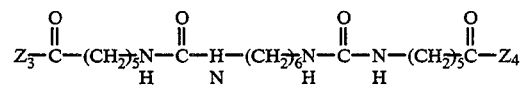

where $Z_3$ and $Z_4$ are

R and R' are $C_5$ aminoalkylene;
X is —$CH_2$—;
m and k are one; and
n is two.

5. A coupling agent according to claim 2 which is

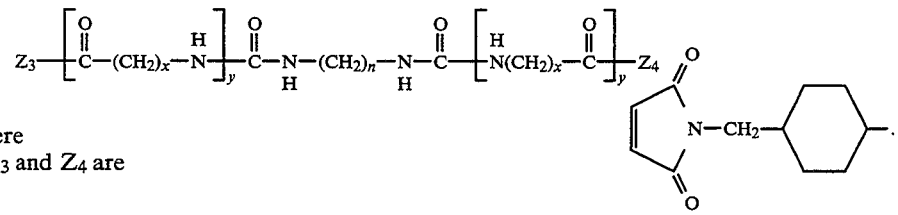

where
$Z_3$ and $Z_4$ are

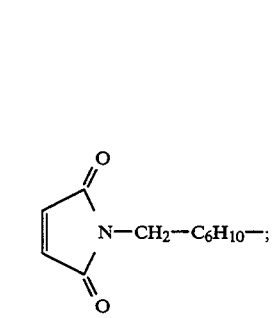

x is an integer from 1 to 10;
y is an integer from 0 to 10; and
n is an integer from 2 to 10.

6. A coupling agent according to claim 5 which is

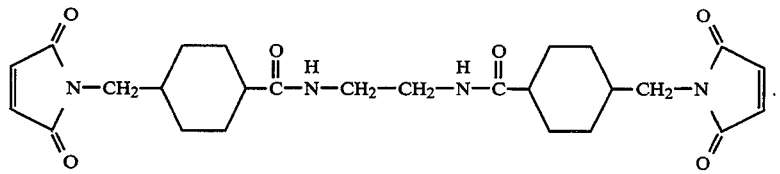

10. A coupling agent according to claim 5 which is

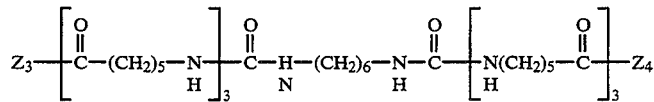

where $Z_3$ and $Z_4$ are

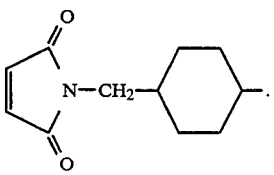

* * * * *